(12) United States Patent
Prusik et al.

(10) Patent No.: US 7,682,830 B2
(45) Date of Patent: *Mar. 23, 2010

(54) PRODUCT SHELF LIFE MONITORING SYSTEMS

(75) Inventors: Thaddeus Prusik, Stroudsburg, PA (US); Allan P. Piechowski, Califon, NJ (US)

(73) Assignee: Temptime Corporation, Morris Plains, NJ (US)

( * ) Notice: Subject to any disclaimer, the term of this patent is extended or adjusted under 35 U.S.C. 154(b) by 739 days.

This patent is subject to a terminal disclaimer.

(21) Appl. No.: 10/457,664

(22) Filed: Jun. 10, 2003

(65) Prior Publication Data

US 2004/0253733 A1    Dec. 16, 2004

(51) Int. Cl.
*G01K 11/00* (2006.01)
*G01K 11/12* (2006.01)

(52) U.S. Cl. .................. 436/2; 422/58; 374/162; 116/216

(58) Field of Classification Search .............. 422/58; 436/2; 374/162; 116/216
See application file for complete search history.

(56) References Cited

U.S. PATENT DOCUMENTS

| | | | | |
|---|---|---|---|---|
| 5,420,000 | A * | 5/1995 | Patel et al. ........... | 430/332 |
| 5,672,465 | A * | 9/1997 | Patel et al. ........... | 430/332 |
| 6,427,922 | B1 * | 8/2002 | Marchand ............ | 235/494 |
| 6,524,000 | B1 * | 2/2003 | Roth .................... | 374/102 |

* cited by examiner

*Primary Examiner*—Lyle A Alexander
(74) *Attorney, Agent, or Firm*—K&L Gates LLP

(57) ABSTRACT

A product shelf life monitoring system comprises a label substrate bearing upon a limited portion of its area an active indicator composition responsive to varying temperature over time to effect a visible change in color density or the like. The susceptibility of the indicator composition to similarly respond to incidence of vagrant ultraviolet light is ameliorated by application of an area of ultraviolet light absorbent composition in register above the indicator composition and extending at most only slightly beyond the periphery of the area of indicator composition. In this manner, the remaining area of the label is preserved for ultraviolet light responsive implementations, and only a minimal, economical amount of ultraviolet light absorbent composition is expended.

23 Claims, 3 Drawing Sheets

(a)  (b)

PRODUCT SHELF LIFE MONITORING SYSTEMS

BACKGROUND OF THE INVENTION

The present invention relates to systems, and elements, components, and compositions therefor, for monitoring and indicating the elapse of a predetermined integral of ambient conditions, such as time, temperature, humidity, actinic radiation, vaporous atmosphere, and the like, to which such a system has been exposed. Typically, for example in monitoring a thermal ambient, a composition comprising an indicator system is formulated to exhibit a readily discernible property variation, such as a change of color or color density, upon the elapse of a given time-temperature integral, and the system, often in the form of a label, is associated with a product of foodstuff, medicament, or the like the useful shelf life, i.e., the safe or potent utility, of which is known to expire substantially concurrently with the elapse of the given time-temperature integral.

In particular, the present invention relates to improvements in ambient-condition responsive compositions of shelf life systems comprising substituted diacetylenic monomer components which exhibit a distinct color change as a result of and generally concomitant with a solid state polymerization effected by an ambient condition integral; typically, as in the case of a time-temperature indicator (TTI) system, the integral of time and temperature.

Substituted diacetylenic monomers useful in the present invention have been studied and utilized in TTI systems for many years. Such utility of numerous monomers comprising at least two conjugated acetylene groups (—C≡C—C≡C—) and their unique physico-chemical properties, e.g., responsiveness to temperature change by transforming into contrastingly colored solid state polymerization reaction products, have, for instance, been described by Patel et al. (U.S. Pat. No. 3,999,946). The synthesis of these monomers and their implementation in useful TTI and other shelf life indicator compositions are discussed there at length by Patel et al, and continue to be valid in formulating embodiments of the present invention. Likewise, the use of these diacetylenic monomer shelf life system components and improvements thereon, including asymmetric substitutions and complexes, and improved methods of monomer synthesis, have been described at length by Patel (U.S. Pat. No. 4,384,980) and Preziosi et al. (U.S. Pat. No. 4,788,151). Such useful descriptions and examples of diacetylenic monomer components useful in the present invention are incorporated herein by reference.

While the consistent and predictable response of these diacetylenic monomer compositions to thermal stimuli provides a basis for highly functional and reliable TTI system products, a similar contemporary color-generating solid state polymerization response to other ambient actinic stimuli, such as ultraviolet radiation, significantly compromises their utility in such systems. This detraction has been recognized long since even by Patel et al who suggested the use of active ultraviolet light-absorbing compounds, such as benzophenones, benzotriazoles, and the like to mitigate these results. Thus, diacetylenic monomer composition TTI products comprising sheet elements, such as labels or marker tabs, bearing a localized deposit of active monomer indicator composition have had laminated thereto an overlying film comprising a UV-absorbing composition.

BRIEF SUMMARY OF THE INVENTION

While such a fabrication practice has provided a TTI product with significantly reduced sensitivity to UV stimuli, the expanse of UV-blocking film usually far exceeds that needed to cover the relatively small deposit of active TTI composition component. As a result, a significant amount of expensive UV-absorber composition utilized in the fabrication process serves no advantageous purpose and merely represents a wasted cost factor resource. Further, in some TTI product applications the complete expanse of UV-blocking material prevents the selective employment of otherwise useful areas of a TTI label.

The present invention can obviate the noted shortcomings and disadvantages of prior diacetylenic monomer composition TTI system products and provide such products which yield effective and improved results while reducing costs and achieving significant savings in fabrication time and material resources.

The invention provides a product shelf life monitoring system comprising a substrate surface bearing upon a portion of its area an active indicator composition responsive in a visible change under incident thermal and ultraviolet light energy to at least one of which an associated product is susceptible. The system comprises visibly transparent means disposed between the indicator composition and the source of incident ultraviolet light to intercept and ameliorate the effects of the incident ultraviolet light upon the indicator composition. The ultraviolet light intercepting means can comprise a layer of visible-transparent, ultraviolet light-absorbent composition. Also, the ultraviolet light intercepting means can be closely proximate and at least substantially co-extensive with the indicator composition and can be situated within the portion of the substrate surface bearing the active indicator composition.

In one embodiment, the invention provides a product shelf life monitoring system comprising a label substrate bearing upon a portion of its area an active indicator composition responsive to varying temperature over time to effect a visible change in color density or the like. The susceptibility of the indicator composition to similarly respond to incidence of vagrant ultraviolet light can be ameliorated by application of an area of ultraviolet light absorbent composition in register above the indicator composition and extending at most only slightly beyond the periphery of the area of indicator composition. In this manner, the remaining area of the label can be preserved for ultraviolet light responsive implementations, and only a minimal, economical amount of ultraviolet light absorbent composition need be expended.

In order to provide the noted protection from anticipated vagrant exposure to actinic ultraviolet light during label use, the fabrication process has typically included a "downstream" station at which a continuous web of transparent film bearing a UV-absorbent, or UV-blocker, composition is laminated upon the printed, active monomer face of the label substrate web. To ensure thorough coverage of UV-absorbent composition upon active monomer depositions, the overlay film is normally applied coextensive with the substrate web. A subsequent, final operation in the fabrication stream may be utilized to die-cut and remove extraneous adhesive-backed substrate and overlay film, leaving the desired multiplicity of individual TTI labels on the release sheet backing support web. Along with the excess areas of UV-blocker composition remaining on each label surface, the extraneous overlay film material discarded in this final fabrication operation represents substantial waste of this composition which amounts to a significant component of product cost.

In a preferred embodiment of the present invention, a printing or coating station is situated downstream from the point of active diacetylenic monomer composition application and effects deposition of UV-blocker composition directly upon and in substantial register with the active monomer deposition to provide the latter component optimum protection from incident UV radiation. As in the past, additional printing stations may be provided in the fabrication process for application of desired indicia, such as reference color patches, use instructions, and advertising.

The selective location, according to the invention, of UV-blocker composition only over those areas occupied by active monomer provides additional advantages beyond the direct saving in cost of otherwise wasted UV-absorbent composition. Since, in this improvement, the major extent of the label area is devoid of UV-blocker, indicia may be applied to various portions of that area at a later time and at a greater rate and diversity, and thus more economically, by means of UV-cured printing inks.

Further, and of particular significance in expanding the capabilities of the diacetylenic monomer compositions into multiple response indicator systems, portions of a label face outside the UV-blocker protected TTI site may be employed as sites for indicators, including selected diacetylenic monomer compositions, dedicated as responsive to UV-radiation, thereby incorporating into a single label indicators for both time-temperature and time-radiation integrals relevant to the shelf life of an associated product.

BRIEF DESCRIPTION OF THE DRAWING

The present invention will be described with reference to the accompanying drawing of which.

DESCRIPTION OF THE INVENTION

Figure 1:
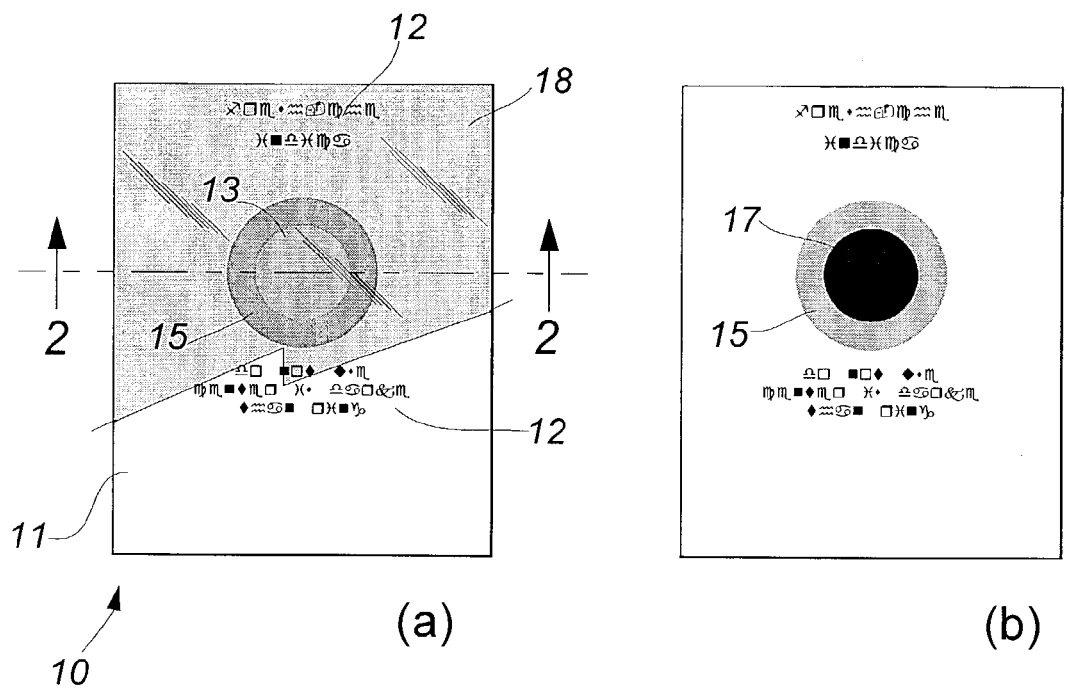
FIG. 1 depicts in plan view the general conformation and functional response of a time-temperature indicator (TTI) system device of the prior art typically comprising an active diacetylenic monomer indicator composition and a UV-protective overlay film.

As seen in FIG. 1(a), a TTI system label 10 of the prior art typically comprises a self-adhesive substrate 11 upon which is printed a spot 13 of active diacetylenic monomer indicator composition. A threshold reference color body, such as shown in the form of a ring 15 surrounding spot 13, is printed in close proximity to the active indicator composition and is provided in a color tone closely approximating the color density which will be developed in indicator spot 13 upon accumulation of the time-temperature integral predetermined to be representative of the shelf-life beyond which the intended associated product, e.g., a foodstuff, such as fish or fowl, or a medicament, such as vaccine or medicine, is expected to lose its utility or potency. As an example of such an expired shelf-life, the indicator composition spot 17 of the label in FIG. 1(b) is shown to have polymerized under the influence of ambient temperature beyond the threshold integral period to yield a tone which is far darker than that of reference color ring 15.

The TTI label product may generally bear additional indicia 12 presenting identifying or instructional text and the like. Further, in order to mitigate the effect of incident UV-light on active indicator composition 13, a sheet of transparent film 18, a section only of which is shown in FIG. 1(a), bearing a UV-absorbent blocker composition has often been coextensively laminated to the face of label substrate 11.

Figure 2:
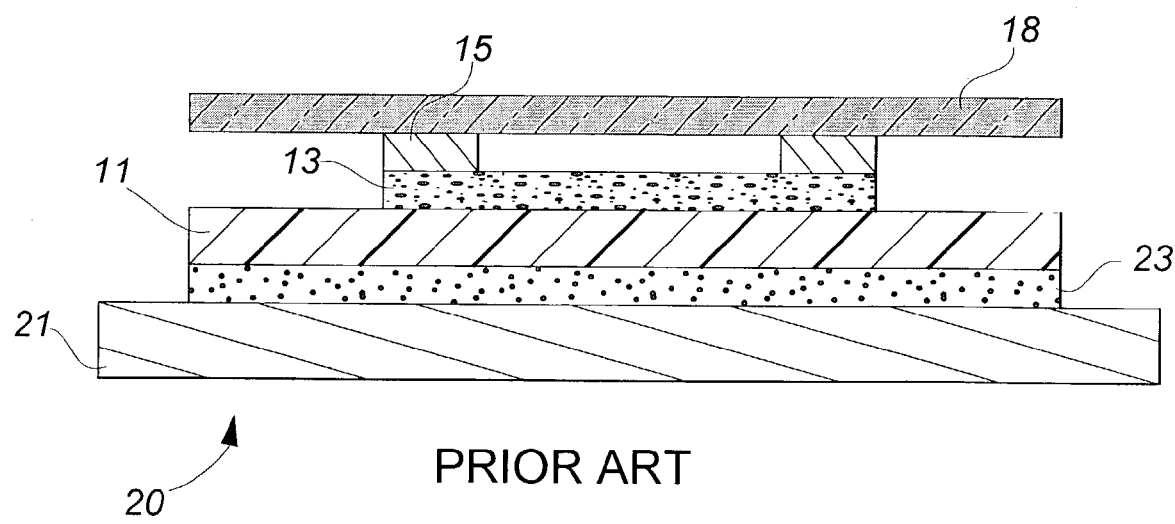
FIG. 2 depicts in elevational cross-section, taken at 2-2 in FIG. 1(a), the structure of the prior art TTI system device.

FIG. 2 depicts in greater detail a typical construction of the prior art TTI label of FIG. 1. Such a label 20 comprises a release sheet 21 support for label substrate 11 of stable paper or film, e.g., biaxially oriented polypropylene, and its pressure-sensitive self-adhesive coating 23. The selected area, or spot, 13 of active diacetylenic monomer indicator composition is deposited on substrate 11, preferably as an ink or lacquer in a screen, gravure, or other printing operation. A body of reference color, such as a registered ring 15, is printed upon composition 13 to provide a means of ready comparison with polymerization color density level during progression of the target shelf-life. After application of additional desired indicia (not shown), UV-blocking overlay film 18 is laminated, preferably by means of an integral self-adhesive layer (not shown), upon the resulting composite label device.

Figure 3:
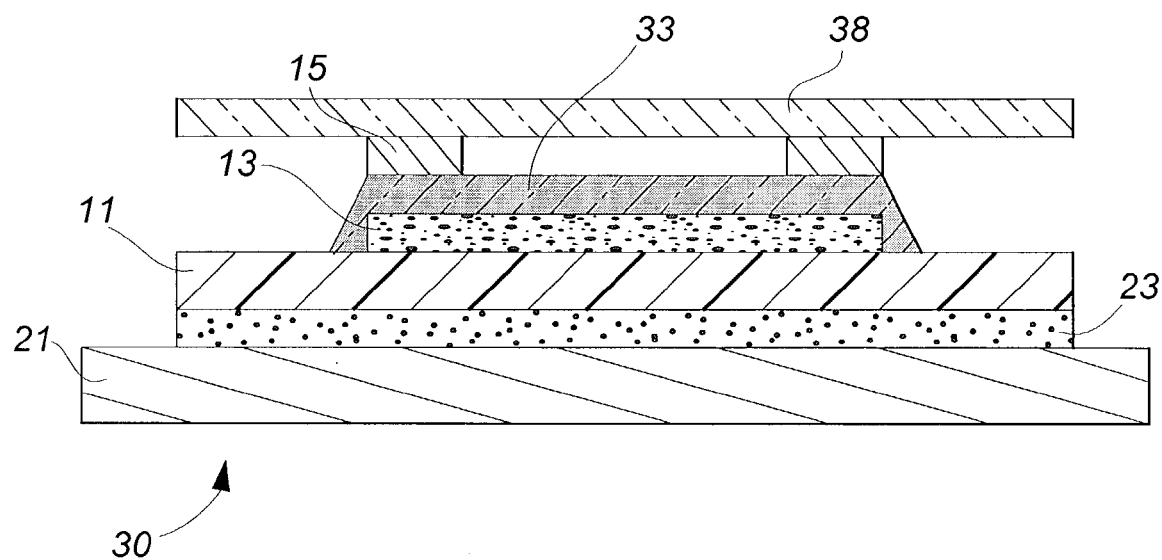
FIG. 3 depicts in elevational cross-section, taken at 3-3 in FIG. 4, the structure of a TTI system device embodying the present invention.

In contrast to the foregoing structure of the prior art, the TTI system label 30 of the present invention is fabricated in a manner to yield the device depicted in FIG. 3. While similar release sheet support web 21 and self-adhesive label substrate 11, 23 materials may be employed to carry the active indicator spot 13 of diacetylenic monomer composition, the present invention departs from past practice by applying a UV-blocking component layer 33, preferably as a printed UV-absorbent transparent lacquer ink composition, directly over active monomer component 13. The area of applied layer 33 may be in precise register with that of active spot 13; however, the simpler application may preferably be such that layer 33 extends to some degree beyond the area of monomer 13 to thus obviate concern of excessive and costly register control parameters. Such application provides the additional benefit of encompassing the monomer deposition with UV-blocker to minimize lateral exposure to vagrant radiation. In this manner, the UV-sensitive monomer component of the TTI system label is accorded optimum protective coverage with UV-blocker composition 33 while requiring only a minimum amount of such composition and avoiding in great measure the previously encountered costly waste.

Figure 4:
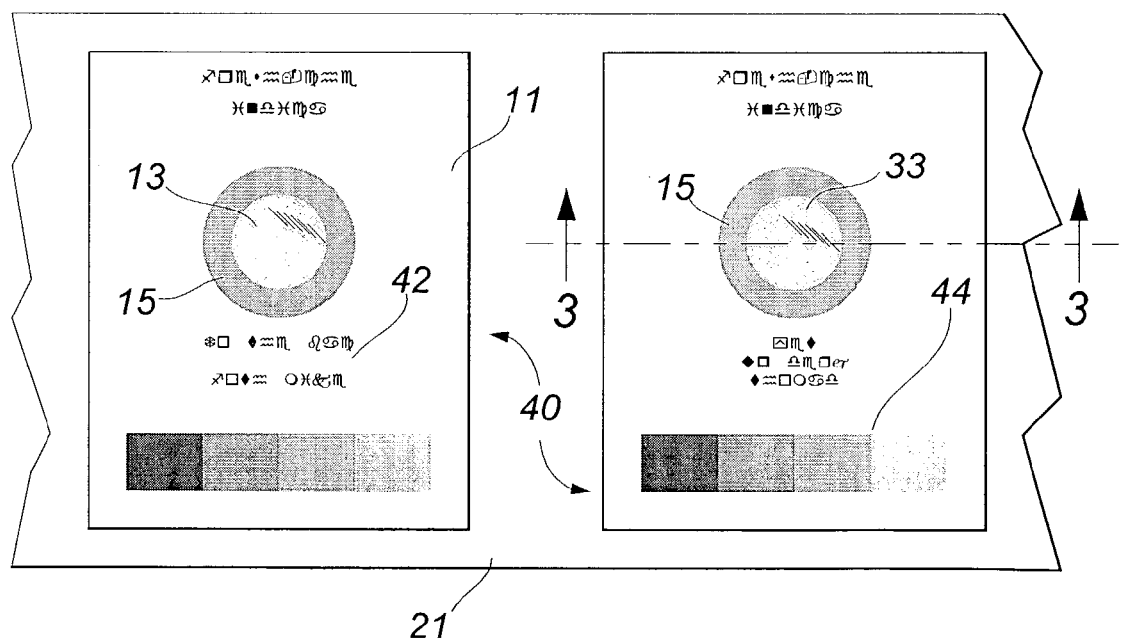
FIG. 4 depicts in plan view multiple TTI system devices embodying the present invention.

A color contrast comparison reference component 15 may be printed in turn with other desired indicia according to prior practice, but with the advantageous exception that improved and highly preferred UV-setting compositions and inks may now be employed without concern of deleteriously affecting the active monomer indicator composition with processing UV light. The utility of reference component ring 15 remains as with prior TTI labels in that, as seen in FIG. 4, the color density change progression of indicator 13 may be observed at any time through visible-transparent UV-blocker film 33 revealed at the annular opening in reference ring 15. As an optional component to provide protection from physical abrasion or abuse, substantially inert, transparent film 38 may be applied over the label product in the manner previously employed with a UV-blocker overlay film 18.

In addition to a capability for subsequent application of printed indicia 42, such as point-of-sale information, in label areas now unobstructed by UV-blocker, a further advantageous embodiment afforded by the invention may be seen in FIG. 4 which generally depicts a multiplicity of TTI system labels 40 as typically arranged in series during continuous printed fabrication on a section of carrier web 21. Areas of label substrate 11 not otherwise occupied by active TTI components, and being devoid of UV-blocking composition, are now available to support active components of a responsive system, represented generally at 44, for indicating an integral of time and UV-light exposure, that is, one constituting an indicator of shelf life vis-à-vis ultraviolet light to which an associated foodstuff or other product may, along with excessive heating, be susceptible. The limited and localized disposition of UV-absorbent composition achieved in systems of the present invention has enabled such expanded and complementary indicator utility.

Representative implementations of the present invention may be seen more specifically in the following examples.

Example I

An active TTI system indicator composition comprising a commonly used substituted diacetylenic monomer was prepared by first ball milling about 9.0 parts by weight of 2,4-hexadiyn-1,6-bis (ethylurea) and 25 parts n-butanol for about 16 hours to obtain a fine particle dispersion which was then mixed with a lacquer solution of about 8.3 parts of ethyl cellulose and 60 parts n-butanol. The mixture was then thinned to a desired printing ink consistency with up to about 85 parts of n-butanol.

A UV-blocker ink composition of printable consistency was prepared by thoroughly mixing about 3.5 parts by weight of 2-2' dihydroxy-4-methoxybenzophenone, which is an organic UV blocker compound, 2.5 parts Orosol Yellow dyes and 2.1 parts zinc oxide, which is an inorganic UV-blocker compound, into a lacquer base prepared with about 18.4 parts nitrocellulose, 5.0 parts 2-ethylhexyl-2-cyano-3,3-diphenyl acrylate, and 1 part silicone-based flow adjunct in a solvent mixture of about 45 parts ethyl-3-ethoxy propionate, 5.7 parts isopropanol, 11.4 parts ethyl acetate, and 5.4 parts diacetone alcohol.

The above indicator ink composition was printed as a series of spot images of about 6 mm diameter on a first length of continuous strip substrate web of white-pigmented biaxially oriented polypropylene in a Gallus R250 (Gallus, Inc., Philadelphia, Pa.) rotary screen printing press utilizing a 39%, 180 µm screen. A second length of substrate web was likewise printed with indicator composition, and at a subsequent press station the buff-colored indicator spots were over-printed in similar manner with the above UV-blocker ink as substantially registered images of about 8 mm diameter. Samples were taken from the two printings for comparative testing in the following manner.

Sample sections (A and B) were taken from the first length of printed strip web without UV-blocker overprint. Sample (A) was sealed within an opaque foil envelope for use as a control and sample (B) was retained for use as is. A third sample (C) was taken from the second length of printed web having UV-blocker overprint for use as is. These samples and control were exposed together to mid-day sunlight (at about 22° C. and 25% relative humidity) with measurements of indicator spot color density being taken at regular intervals with a commercial reflection densitometer (X-Rite 404) operating in the cyan mode until a predetermined threshold color density of a sample was observed.

Figure 5:
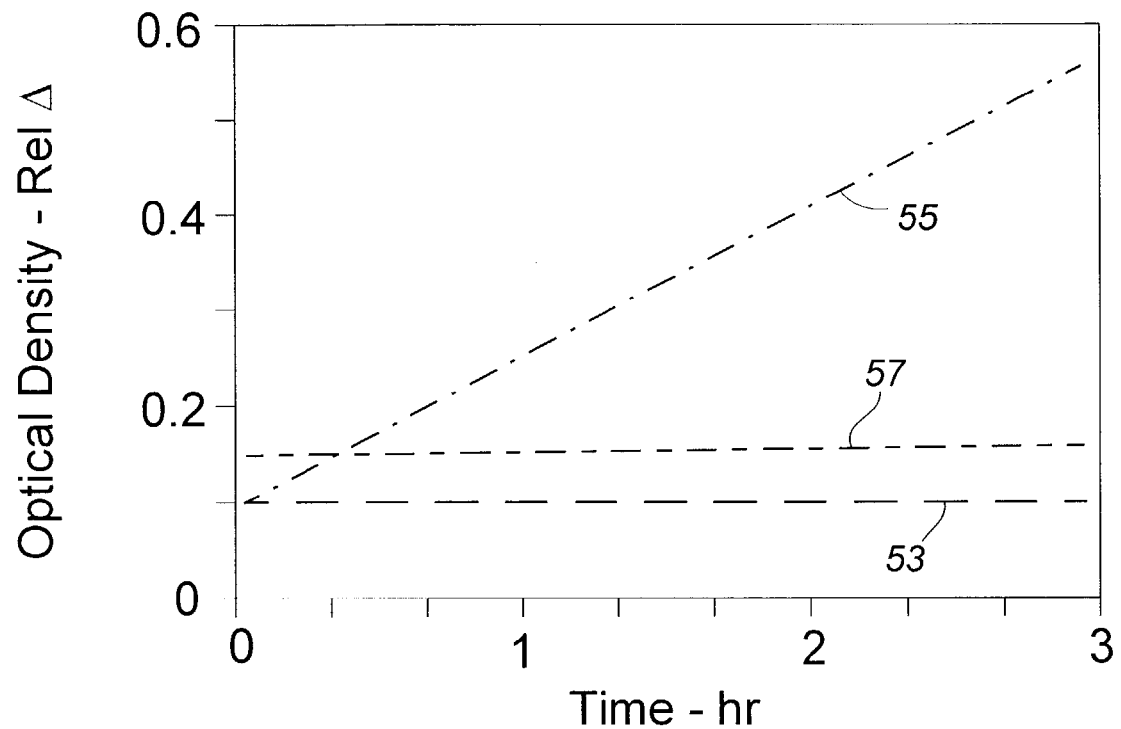
FIG. 5 presents graphic data depicting the UV-protective efficacy of a device embodying the present invention.

Results of these tests are shown in FIG. 5 as traces of the relative color density change data. As anticipated, data 53 of the enclosed control sample (A) showed no color density change. Data 55 of the unprotected sample (B) indicator spots showed an increase in color density at a regular rate to a final dark blue-black during the nearly 3 hour test period, thus confirming the susceptibility of the active indicator composition to the polymerizing influence, at least in part, of ultraviolet light. Data 57 of indicator sample (C) comprising UV-blocker overprint according to the invention, on the other hand, showed substantially no change in color density during the test period, thereby indicating the high efficacy of the overprint embodiment. The offset of these latter data from those of control sample (A) are attributable to the color initially imparted by UV-blocker composition dyes.

Example II

The comparative efficacy of the present invention and the prior art with respect to exposure over a more limited wavelength range of ultraviolet light, such as would normally be encountered in artificial lighting of refrigerated foodstuff display counters, was tested in the following manner. Samples (D and E) of plain and UV-blocker overprinted active indicator composition were prepared in the manner of Example I with the exception of utilizing as the active substituted diacetylenic monomer component a co-crystallized 2:1 mixture of 2,4-hexadiyn-1,6-bis (ethylurea) and 2,4-hexadiyn-1, 6-bis(propylurea). A comparative sample (F) according to the prior art was prepared by laminating a commercial UV-blocker film over a portion of sample (D) plain active indicator composition web material.

Figure 6:
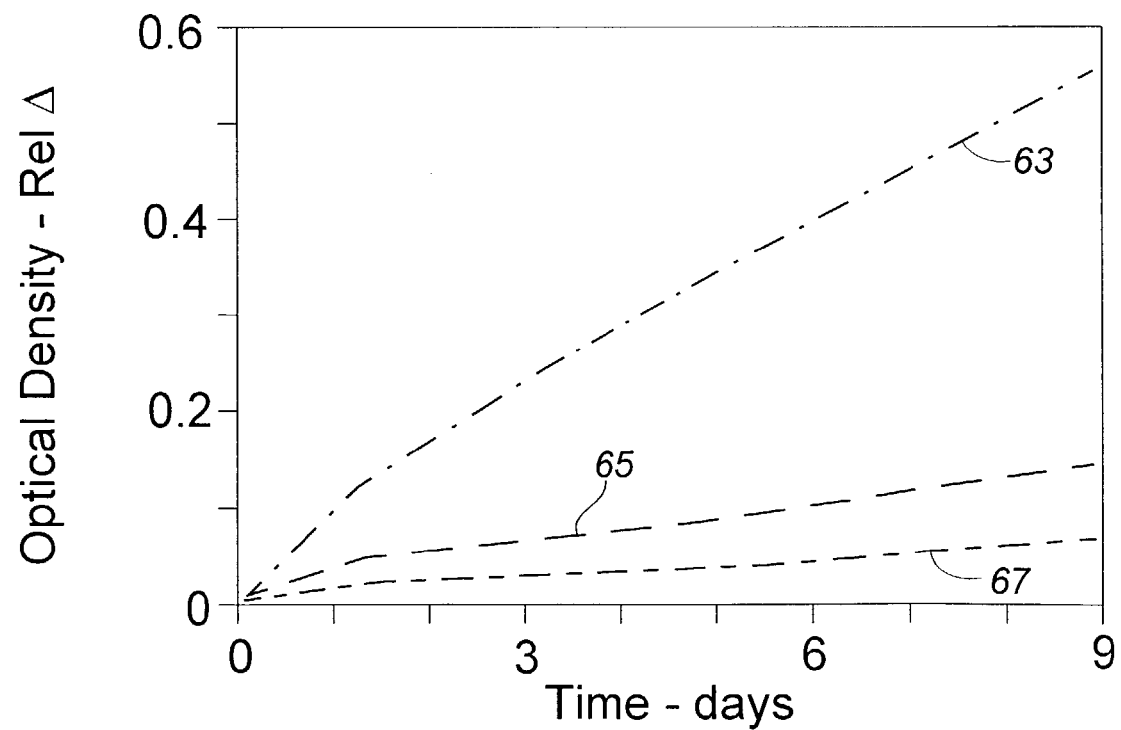
FIG. 6 presents graphic data depicting the comparative UV-protective efficacy of a device embodying the present invention and one of the prior art.

The prepared samples were exposed to about 2800 lux under a fluorescent light fixture in a constant ambient of about 4° C. to substantially simulate storage in a commercial food market display case. As in Example I, regular measurements were made of active indicator composition color density and the relative color density change data were plotted to provide the results shown in FIG. 6. The substantially regular increase in UV-initiated color density in plain sample (D) is represented in the data of trace 63 and is seen to reach a maximum during the 9 day test period. The limited increase in color density of the prior art sample during the same period in overlay-protected sample (F) is shown in the data of trace 65, while trace 67 data from sample (E) shows the lesser rate of UV-initiated color increase achieved by the greater efficacy of the present invention arrangement.

Other TTI system label devices were prepared according to the present invention utilizing various monomer components described in the above-noted patent specifications to achieve a range of time-temperature integral endpoints representative of numerous foodstuff and medicament shelf lives. In each instance, in addition to the readily calculable savings in reduced materials waste, the devices responded with improved efficacy as compared with prior art products.

Through incorporation of integral elements for isolating actinic stimuli, the invention can provide means for achieving TTI systems and compositions that are durable, sensitive, and responsive, which yield significant functional and economic improvements and reduce the consumption of highly priced components and resources.

It is anticipated that other embodiments and variations of the present invention will become readily apparent to the skilled artisan in the light of the foregoing description and examples, and such embodiments and variations are intended to likewise be included within the scope of the invention as set out in the appended claims.

What is claimed is:

1. A product shelf life monitoring system comprising:
   a substrate having a substrate surface, the substrate surface having an occupied surface portion and an unoccupied surface portion contiguous with the occupied surface portion;
   an active indicator composition supported on the occupied surface portion, the unoccupied surface portion being free of active indicator composition, the active indicator composition being responsive with a visible change to incident thermal energy and to ultraviolet radiation, an associated product being susceptible to at least the thermal energy; and
   a layer of a visibly transparent, ultraviolet-blocker ink composition disposed between said indicator composition and the source of said incident ultraviolet radiation to intercept and ameliorate the effects of said incident ultraviolet radiation upon said indicator composition;
   wherein said ultraviolet-blocker ink composition layer is at least co-extensive with said active indicator composition and is situated entirely within said occupied surface portion of said substrate surface area and said unoccupied surface portion is not covered by the ultraviolet radiation-absorbent layer;
   wherein said active indicator composition comprises an indicator ink printed upon said substrate;
   wherein said ultraviolet-blocker ink composition is overprinted on said substrate over said indicator ink and comprises a lacquer base, 2-2'-dihydroxy-methoxybenzophenone, zinc oxide, and orasol yellow dye and a liquid vehicle.

2. A system according to claim 1 wherein said associated product is a foodstuff.

3. A system according to claim 1 wherein said associated product is a medicament.

4. A system according to claim 1 wherein said ultraviolet blocker composition can absorb ultraviolet light and comprises one or more active components selected from the group consisting of benzophenones, benzotriazoles dihydroxy-4-methoxybenzophenone and zinc oxide.

5. A product shelf life monitoring system according to claim 1 wherein said associated product is selected from the group consisting of fish, fowl, vaccine and medicine.

6. A product shelf life monitoring system according to claim 1 wherein the substrate comprises a label and the unoccupied portion of the substrate surface area comprises a major extent of the label.

7. A product shelf life monitoring system according to claim 1 wherein said ultraviolet radiation-absorbent layer extends beyond the area of said indicator composition.

8. A product shelf life monitoring system according to claim 1 wherein said ultraviolet radiation-absorbent layer registers with said indicator composition and has an area greater than the area of said indicator composition by not more than 78% of the area of said indicator composition.

9. A product shelf life monitoring system according to claim 1 comprising printed indicia printed with an ultraviolet-curable ink, the printed indicia optionally comprising a reference component having an appearance intended to be compared with the appearance of the indicator composition.

10. A product shelf life monitoring system according to claim 1 comprising a reference component printed on the ultraviolet-blocker ink composition layer, the reference component being printed with an ultraviolet-curable ink and having an appearance to be compared with the appearance of the indicator composition.

11. A system according to claim 1 wherein the ultraviolet-radiation-absorbent ink composition comprises a binder, the organic ultraviolet-radiation absorbent compound is soluble in the liquid vehicle, and the inorganic ultraviolet-radiation absorbent compound is insoluble in the liquid vehicle.

12. A system according to claim 1 wherein the ultraviolet-radiation-absorbent ink composition comprises a benzophenone, zinc oxide, nitrocellulose and a solvent mixture wherein the benzophenone is soluble in the solvent mixture and the zinc oxide is insoluble in the solvent mixture.

13. A system according to claim 1 wherein said active indicator composition comprises a substituted diacetylenic monomer comprising at least two conjugated acetylenic groups.

14. A system according to claim 13 wherein said substituted diacetylenic monomer is selected from the group consisting of symmetrically substituted mono- and bis-urethane and urea derivatives, asymmetrically substituted mono- and bis-urethane and urea derivatives, 2,4-hexadiyn-1,6-bis(ethylurea), a co-crystallized mixture of 2,4-hexadiyn-1,6-bis(ethylurea) and 2,4-hexadiyn-1,6-bis(propylurea).

15. A product shelf life monitoring system according to claim 1 wherein said substrate surface bears upon a portion of its area situated outside said portion a second active indicator composition responsive in a visible change under incident ultraviolet light-energy to which an associated product is susceptible.

16. A product shelf life monitoring system according to claim 15 wherein said second active indicator composition comprises a substituted diacetylenic monomer comprising at least two conjugated acetylene groups.

17. A multiplicity of product shelf life monitoring system labels for monitoring the shelf life of associated product items, the associated product being susceptible to thermal energy and the labels being supported on a continuous carrier web suitable for printing, wherein each shelf life monitoring system label comprises:
   (a) a label substrate having a surface, the surfaces of the multiplicity of labels being coextensively overlayable by a film;
   (b) an area of active indicator composition located on each label substrate surface, the active indicator composition being responsive with a visual change to incident thermal energy and to incident ultraviolet radiation; and
   (c) a layer of a visibly transparent, ultraviolet-blocker ink composition disposed between a source of incident ultraviolet radiation and each said area of indicator composition to intercept and ameliorate the effects of said incident ultraviolet radiation upon said indicator composition;
   wherein each area of active indicator composition occupies a portion of the respective label substrate surface, each label substrate surface comprises an unoccupied surface portion free of active indicator composition and contiguous with the occupied surface portion,
   wherein said ultraviolet-blocker ink composition layer comprises multiple ultraviolet-blocker ink composition areas,
   wherein each ultraviolet-blocker ink composition area is at least co-extensive with each said indicator composition area, is situated entirely within the occupied portion of the label substrate surface, and said unoccupied portion of the label substrate surface is not covered by the ultraviolet-blocker ink composition layer,
   wherein the indicator composition comprises an ink
   wherein the ultraviolet-blocker ink composition is overprinted on said substrate over said indicator ink and comprises a lacquer base, 2-2'-dihydroxy-methoxybenzophenone, zinc oxide, an orasol yellow dye and a liquid vehicle; wherein the unoccupied portion of each label substrate surface comprises a major extent of each label substrate surface, and
wherein the ultraviolet-blocker ink composition layer comprises multiple zones and each zone registers with each respective area of indicator composition, extends beyond each respective area of indicator composition and has an area greater than the area of the indicator composition by not more than 78% of the area of the indicator composition.

18. A multiplicity of product shelf life monitoring system labels according to claim 17 comprising a reference component printed on the ultraviolet-blocker ink composition layer, the reference component being printed with an ultraviolet-curable ink and having an appearance intended to be compared with the appearance of the indicator composition.

19. A multiplicity of product shelf life monitoring system labels according to claim 17 comprising a protective transparent film overlying the label substrates coextensively with the label substrates.

20. A multiplicity of product shelf life monitoring system labels according to claim 19 wherein the unoccupied portion of each label substrate surface comprises a major extent of each label substrate surface.

21. A multiplicity of product shelf life monitoring system labels according to claim 19 wherein the ultraviolet-blocker ink composition layer extends beyond each respective area of indicator composition.

22. A multiplicity of product shelf life monitoring system labels according to claim 19 wherein the ultraviolet-blocker ink composition layer comprises multiple zones and each zone resisters with a respective indicator composition area and has an area greater than the area of the indicator composition by not more than 78% of the area of the indicator composition.

23. A method of making a product shelf life monitoring system comprising a substrate surface having an occupied surface portion bearing an active indicator composition and an unoccupied surface portion free of active indicator composition and contiguous with the occupied surface portion, the active indicator composition being responsive with a visible change to incident thermal energy and to ultraviolet radiation, an associated product being susceptible to at least the thermal energy, said system comprising a layer of a visibly transparent, ultraviolet-blocker ink composition disposed between said indicator composition and the source of said incident ultraviolet radiation to intercept and ameliorate the effects of said incident ultraviolet radiation upon said indicator composition, wherein said ultraviolet-blocker ink layer is at least co-extensive with said active indicator composition, is situated entirely within said occupied surface portion of said substrate surface area and said unoccupied surface portion is not covered by the ultraviolet-blocker ink layer the method comprising:
  printing an active indicator composition on the substrate surface to form the occupied surface portion bearing an active indicator composition; and
  printing a visibly transparent ultraviolet-blocker ink on to the active indicator composition on the substrate to form the layer of visibly transparent, ultraviolet-blocker ink composition, the ultraviolet-blocker ink comprising, a lacquer base, 2-2'-dihydroxy-methoxybenzophenone, zinc oxide, and orasol yellow dye and a liquid vehicle.

* * * * *